(12) United States Patent
Hirasawa et al.

(10) Patent No.: US 10,240,215 B2
(45) Date of Patent: Mar. 26, 2019

(54) METHOD FOR PRODUCING ASTAXANTHIN BY FERMENTATION

(71) Applicant: JX Nippon Oil & Energy Corporation, Tokyo (JP)

(72) Inventors: Kazuaki Hirasawa, Tokyo (JP); Hiroshi Satoh, Tokyo (JP); Hisashi Yoneda, Tokyo (JP); Tetsuhisa Yata, Tokyo (JP); Mitsutoshi Azuma, Tokyo (JP)

(73) Assignee: JX Nippon Oil & Energy Corporation, Tokyo (JP)

( * ) Notice: Subject to any disclaimer, the term of this patent is extended or adjusted under 35 U.S.C. 154(b) by 103 days.

(21) Appl. No.: 15/293,985

(22) Filed: Oct. 14, 2016

(65) Prior Publication Data
US 2017/0029862 A1 Feb. 2, 2017

Related U.S. Application Data

(63) Continuation of application No. 13/634,657, filed as application No. PCT/JP2011/056033 on Mar. 15, 2011, now Pat. No. 9,605,323.

(30) Foreign Application Priority Data

Mar. 15, 2010 (JP) ................. 2010-057321

(51) Int. Cl.
| | | |
|---|---|---|
| *C12N 1/20* | (2006.01) | |
| *C12R 1/01* | (2006.01) | |
| *C12P 23/00* | (2006.01) | |
| *C12N 1/38* | (2006.01) | |
| *A23K 20/179* | (2016.01) | |
| *A23K 50/80* | (2016.01) | |
| *A23K 50/75* | (2016.01) | |

(52) U.S. Cl.
CPC .............. *C12R 1/01* (2013.01); *A23K 20/179* (2016.05); *A23K 50/75* (2016.05); *A23K 50/80* (2016.05); *C12N 1/20* (2013.01); *C12N 1/38* (2013.01); *C12P 23/00* (2013.01); *C12N 2500/02* (2013.01)

(58) Field of Classification Search
None
See application file for complete search history.

(56) References Cited

U.S. PATENT DOCUMENTS

| | | |
|---|---|---|
| 5,356,810 A | 10/1994 | Fleno et al. |
| 5,607,839 A | 3/1997 | Tsubokura et al. |
| 6,706,278 B1 | 3/2004 | Tsubokura et al. |
| 9,605,323 B2 | 3/2017 | Hirasawa et al. |
| 2003/0044886 A1* | 3/2003 | Tsubokura ............. C12P 23/00 435/67 |
| 2006/0053513 A1 | 3/2006 | Steiger et al. |
| 2006/0234333 A1 | 10/2006 | Matuschek et al. |
| 2007/0054351 A1 | 3/2007 | Zhang |
| 2008/0060096 A1 | 3/2008 | Sauer et al. |
| 2009/0298146 A1 | 12/2009 | Choi et al. |

FOREIGN PATENT DOCUMENTS

| | | |
|---|---|---|
| EP | 1138208 | * 10/2001 |
| EP | 1138208 A4 | 8/2004 |
| EP | 2157168 A4 | 6/2010 |
| JP | 07-79796 A | 3/1995 |
| JP | 09-308481 | 2/1997 |
| JP | 11-69969 A | 3/1999 |
| JP | 2001-095500 A | 4/2001 |
| JP | 2001-512030 A | 8/2001 |
| JP | 2001-352995 A | 12/2001 |
| JP | 2007-97584 A | 4/2007 |
| JP | 2007-143491 A | 6/2007 |
| JP | 2007-143492 A | 6/2007 |
| JP | 2007-244205 A | 9/2007 |
| JP | 2007-244222 A | 9/2007 |
| JP | 2008-167665 A | 7/2008 |
| RU | 2005125072 A | 6/2006 |
| WO | WO-99/06586 A1 | 2/1999 |
| WO | WO-2004029261 A3 | 5/2004 |
| WO | WO-2005/118812 A1 | 12/2005 |
| WO | WO-2011115099 A1 | 9/2011 |

OTHER PUBLICATIONS

Shull et al., J. Biol. Chem. 142: 913-920 (1942).*
Somerville et al., BMC Microbiol. 13(9): 1-2 (2013).*
Water Quality with Vernier, http://www2.vernier.com/sample_labs/WQV-05-COMP-dissolved_oxygen.pdf, accessed Feb. 4, 2014.*
Ming-jun, Zhu, et al., "Effects of Biotin on Cell Growth and Astaxanthin Accumulation of Phaffia Rhodozyma", Journal of South China Unversity of Technology, Jun. 2003, vol. 31, No. 6, pp. 80-84.
Widmer, Erich, "Synthetic Advances in the Caroteriod Filed", Pure and Applied Chemisty, vol. 57, No. 5, 1985, pp. 741-752.
Widmer, Erich, et al., "Technische Verfahren zur Synthese von Carotinoiden und verwandten Verbindungen aus 6-Oxo-isophoron. II. Ein néues Konzept für die Synthese von (3RS, 3' RS)-Astaxanthin1)2", Helvetica Chimica Acta, vol. 644, No. 7, 1981, pp. 2436-2446.

(Continued)

*Primary Examiner* — Erin M. Bowers
(74) *Attorney, Agent, or Firm* — McCarter & English, LLP

(57) ABSTRACT

An object of the present invention is to provide a method for microbioiogically producing astaxanthin of high concentration at low cost while suppressing production of canthaxanthin. Specifically, the present invention relates to a method for producing carotenoids including astaxanthin comprising culturing a bacterium that concurrently produces astaxanthin and canthaxanthin in a medium containing biotin, wherein a ratio of concentration of produced canthaxanthin to concentration of produced astaxanthin in a culture product after the end of culture in the medium is lower than that in a culture product alter the end of culture in a biotin-free medium.

5 Claims, No Drawings

Specification includes a Sequence Listing.

(56) References Cited

OTHER PUBLICATIONS

Lee, Jae Hyung, et al., "*Paracoccus haeundaensis* sp. nov, a Gram-negative, halophilic, astaxanthin-producing bacterium", International Journal of Systematic and Evolutionary Microbiology, vol. 54, 2004, pp. 1699-1702.

Official Journal of the European Communities, Amending the conditions for authorisation of canthaxanthin in feedingstuffs in accordance with Council Directive 70/524/EEC, Jan. 24, 2003, pp. L 22/28-L 22/30.

Tsubokura, Akira, et al., "*Paracoccus carotinifaciens* sp. nov., a new aerobic Gram-negative astaxanthin-producing bacterium", International Journal of Systematic Bacteriology, Jan. 1999, vol. 49, p. 277-282.

Kyowahakko, ed., *Laboratory Manual for Microbiology*, 1987, 3rd printing, pp. 264-265 and partial English translation.

Liggett et al., Corn Steep Liquor in Microbiology, *Bacteriol. Rev.* 1948, 12(4): 297-311.

Ramchandaran et al., Food Technol. Biotechnol. 44(2): 185-195 (2006).

http://web.archive.org/web/20071115040953/http://en.wikipedia.org/wiki/Pol-yhydroxybutyrate, archived Nov. 15, 2007, accessed Aug. 14, 2013.

Nghiem et al., Appl. Biochem. Biotechnol. 57/58: 633-638 (1996).

Water Quality with Vernier, http://www2.vernier.com/sample.sub.--labs/WQV-05-COMP-dissolved.sub.--oxy- gen.pdf, accessed Feb. 4, 2014 (hereinafter 'Vernier').

International Preliminary Report on Patentability relating to International Application No. PCT/JP2011/056033 dated Jun. 7, 2011.

European Search Report based on European Patent Application No. 11756284.3 dated Dec. 22, 2014, which is a foreign counterpart of this application, pp. 1-3.

Russian Notice of Allowance dated Apr. 1, 2016 relating to Russian Counterpart Application No. 2012143727—English Translation Provided.

\* cited by examiner

METHOD FOR PRODUCING ASTAXANTHIN BY FERMENTATION

RELATED APPLICATIONS

This application is a continuation of U.S. application Ser. No. 13/634,657, filed Sep. 13, 2012, which is a national stage application filed under 35 USC § 371 of PCT/JP2011/056033, filed Mar. 15, 2011, which claims the benefit of Japanese Patent Application No. 2010-057321, filed Mar. 15, 2010. The entire contents of each of the above-mentioned applications are incorporated herein by reference in their entirety.

SUBMISSION OF SEQUENCE LISTING

The Sequence Listing associated with this application is filed in electronic format via EFS-Web and hereby incorporated by reference into the specification in its entirety. The name of the text file containing the Sequence Listing is 119244_00110_Sequence_Listing. The size of the text file is 3 KB, and the text file was created on Oct. 6, 2016.

TECHNICAL FIELD

The present invention relates to a method for producing carotenoids, including astaxanthin, by microorganism fermentation.

BACKGROUND ART

Carotenoids are natural pigments that are useful as feed additives, food additives, pharmaceutical agents, and the like. Examples of carotenoids include astaxanthin, canthaxanthin zeaxanthin, β-cryptoxanthin, lycopene, β-carotene, phoenicoxanthin, adonixanthin, echinenone, asteroidenone, and 3-hydroxyechinenone.

Among carotenoids, astaxanthin is useful as feed additives, for example, as a body color-improving agent for cultivated fishes such as salmon, trout, and sea bream or an egg yolk color-improving agent for poultry. Moreover, astaxanthin is highly valuable in the industries as safe natural food additives and health food materials.

Similar to astaxanthin, adonixanthin and phoenicoxanthin are also expected to be used as feed additives, food additives, pharmaceutical agents, and the like once industrial production methods thereof are established. Furthermore, β-carotene is used as feed additives, food additives, pharmaceutical agents, and the like; canthaxanthin is used as feed additives, food additives, cosmetics, and the like; and zeaxanthin is used as food additives, feed additives, and the like. In addition, other carotenoids such as lycopene, echinenone, β-cryptoxanthin, 3-hydroxyechinenone, and asteroidenone are also expected to be used as feed additives, food materials, and the like. Known methods for producing these carotenoids include chemical synthesis methods, methods of extraction from natural sources, and production methods using microorganisms.

As methods for chemically synthesizing astaxanthin, a method utilizing conversion of β-carotene (Non-Patent Document 1) and a method employing synthesis from C15 phosphonium salt (Non-Patent Document 2) are known. Astaxanthin produced by such chemical synthesis methods is commercially available as a feed additive. In addition, since astaxanthin is present in fishes such as sea bream and salmon as well as crustaceans such as shrimp, crab, and krill, it may also be extracted therefrom.

Methods that have been reported for producing astaxanthin using microorganisms include a culture method using green alga *Haematococcus pluvialis* (Patent Document 1), a fermentation method using red yeast *Phaffia rhodozyma* (Patent Document 2), and a fermentation method using a bacterium belonging to the genus *Paracoccus* (hereinafter occasionally referred to as a "*Paracoccus* bacterium").

Examples of astaxanthin-producing *Paracoccus* bacteria include strains E-396 and A-581-1 (Patent Document 3 and Non-Patent Document 3). Examples of other astaxanthin-producing *Paracoccus* bacteria include *Paracoccus marcusii* strain MH1 (Patent Document 4), *Paracoccus haeundaensis* strain BC74171 (Non-Patent Document 4), *Paracoccus* bacterial strain N-81106 (Patent Document 5), and *Paracoccus* sp. strain PC-1 (Patent Document 6).

There have been several problems concerning the above-mentioned carotenoid production methods. For example, chemical synthesis methods have unfavorable impression on consumers from a safety perspective. Extraction from natural sources such as shrimp and crab is associated with high production costs. In addition, production using a green alga or yeast results in low productivity and has difficulty in extraction of a carotenoid therefrom due to strong cell walls thereof.

Meanwhile, bacteria belonging to the genus *Paracoccus* are advantageous in that proliferation rates thereof are fast, carotenoid productivities thereof are high, and carotenoids can readily be extracted therefrom, etc. Several methods for culturing such bacteria have been reported. For example, Patent Document 7 discloses a method characterized by adding an iron salt during culture. Patent Document 8 discloses a method characterized by restricting the carbon source concentration. However, such culture methods are problematic in that large amounts of canthaxanthin accumulate during production of astaxanthin.

Canthaxanthin is a useful feed additive for improving the color tone of salmon meat or hen egg yolk, while the ADI (acceptable daily intake) thereof is limited to 0.03 mg/kg of body weight and the upper limits of the amounts of canthaxanthin acceptable to be added to feed are stipulated as 25 mg/kg and 8 mg/kg for salmon and laying hens, respectively, in Europe (Non-Patent Document 5). Thus, it is necessary to control the canthaxanthin content at a low level when producing astaxanthin using a microorganism. Patent Document 9 discloses a method wherein canthaxanthin production is reduced by controlling the dissolved oxygen concentration. However, such a method also results in significant reduction in the concentration of produced astaxanthin and thus is not practical in terms of production cost.

CITATION LIST

Patent Literatures

Patent Document 1: JP Patent Application Laid-open Publication No. 2007-97584 A
Patent Document JP Patent Application Laid-open Publication No. 11-69969 A (1999)
Patent Document 3: JP Patent Application Laid-open Publication No. 7-79796 A (1995)
Patent Document 4: JP Patent Application Laid-open Publication No. 2001-512030 A
Patent Document 5: JP Patent Application Laid-open Publication No. 2007-244205 A
Patent Document 6: WO 2005/118812
Patent Document 7: JP Patent Application Laid-open Publication No. 2007-143492 A Patent Document 8: JP Patent Application Laid-open Publication No. 2008-167665 A
Patent Document 9: JP Patent Application Laid-open Publication No. 2001-352995 A Non-Patent Literatures Non-Patent Document 1: Erich Widmer et al., "Pure Appl. Chem.," 1985, vol. 57, pp. 741-752
Non-Patent Document 2: Erich Widmer et al., "Helv. Chim. Acta," 1981, vol. 64, pp. 2436-2446
Non-Patent Document 3: Akira Tsubokura et al., "International Journal of Systematic Bacteriology," 1999, vol. 49, pp. 277-282
Non-Patent Document 4: Jae Hyung Lee et al., "International Journal of Systematic and Evolutionary Microbiology," 2004, vol. 54, pp. 1699-1702
Non Patent Document 5: Official Journal of the European Communities L 22/28-30, 25.1.2003

SUMMARY OF INVENTION

Problems to be Solved by the Invention

The present invention has been made in view of the above circumstances. An object of the present invention is to provide a method for microbiologically producing astaxanthin of high concentration at low cost while suppressing production of canthaxanthin.

Means for Solving the Problems

As a result of intensive studies in order to achieve the above object, the present inventors have found that production of highly concentrated astaxanthin can be achieved while maintaining the concentration of produced canthaxanthin at a low level by adding biotin to a medium during culture of a bacterium that concurrently produces astaxanthin and canthaxanthin. This has led to the completion of the present invention.

The present invention encompasses the followings.

(1) A method for producing carotenoids including astaxanthin comprising culturing a bacterium that concurrently produces astaxanthin and canthaxanthin in a medium containing biotin, wherein a ratio or concentration of produced canthaxanthin to concentration of produced astaxanthin in a culture product after the end of culture in the medium is lower than that in a culture product after the end of culture in a biotin-free medium.
(2) The method according to (1), wherein a concentration of biotin in the medium is 0.001 mg/L to 50 mg/L.
(3) The method according to (1), wherein the ratio of concentration of produced canthaxanthin to concentration of produced astaxanthin in the culture product after the end of culture is 25% by mass or less.
(4) The method according to (1), wherein a concentration of produced gluconic acid in the culture product after the end of culture is 30 g/L or less.
(5) The method according to (1), wherein a dissolved oxygen concentration in the culture product is controlled at 1 ppm or more during culture.
(6) The method according to (1), wherein a poly-β-hydroxybutyrate (hereinafter referred to as "PHB") content in the culture product after the end of culture based on dry cells is 30% by mass or less.
(7) The method according to (1), wherein a dissolved oxygen concentration in the culture product is controlled at 1 ppm or more during culture, and the ratio of concentration of produced canthaxanthin to concentration of produced astaxanthin in the culture product after the end of culture is 25% by mass or less.
(8) The method according to (1), wherein a dissolved oxygen concentration in the culture product is controlled at 2 ppm or more during culture, and the ratio of concentration of produced canthaxanthin to concentration of produced astaxanthin in the culture product after the end of culture is 8% by mass or less.
(9) The method according to (1), wherein a dissolved oxygen concentration in the culture product is controlled to increase in a stepwise or continuous manner during culture.
(10) The method according to (1), wherein an initial dissolved oxygen concentration in the culture product is controlled at 1 to 2.5 ppm in the intermediate phase of culture and the dissolved oxygen concentration is increased in a stepwise or continuous manner, and the ratio of concentration of produced canthaxanthin to concentration of produced astaxanthin in the culture product after the end of culture is 25% by mass or less.
(11) The method according to (1), wherein an initial dissolved oxygen concentration in the culture product is controlled at 2 to 3.5 ppm in the intermediate phase of culture and the dissolved oxygen concentration is increased in a stepwise or continuous manner, and the ratio of concentration of produced canthaxanthin to concentration of produced astaxanthin in the culture product after the end of culture is 8% by mass or less.
(12) The method according to (1), wherein the bacterium is a bacterium belonging to the genus *Paracoccus*.
(13) The method according to (1), wherein the bacterium is of a mutant strain having lowered PHB producing ability.
(14) The method according to (1), wherein the bacterium is of a mutant strain having lowered gluconic acid producing ability.
(15) The method according to (1), wherein the bacterium is a bacterium in which the nucleotide sequence of DNA corresponding to 16S ribosomal RNA is substantially homologous to the nucleotide sequence shown in SEQ ID NO: 1.
(16) The method according to (15), wherein the bacterium is of strain E-396 (FERM BP-4283) or A-581-1 (FERM BP-4671) or a mutant strain thereof.
(17) A carotenoid composition for feed comprising carotenoids including astaxanthin produced by the method according to (1), wherein the ratio of concentration of canthaxanthin to concentration of astaxanthin in the produced carotenoids is 25% by mass or less.
(18) The carotenoid composition for feed according to (17), wherein a PHB content in the produced carotenoids including astaxanthin is 30% by mass or less.
(19) A carotenoid composition for food comprising carotenoids including astaxanthin produced by the method according to (1), wherein the ratio of concentration of canthaxanthin to concentration of astaxanthin in the produced carotenoids is 8% by mass or less.

This description includes part or all of the contents as disclosed in the description and/or drawings of Japanese Patent Application No. 2010-057321, which is a priority document of the present application.

Effects of the Invention

According to the present invention, astaxanthin of high concentration can be microbiologically produced at low cost be keeping the canthaxanthin concentration at a low level. Carotenoids produced by the present invention are useful as feed and food materials.

EMBODIMENTS FOR CARRYING OUT THE INVENTION

Hereinafter, the present invention will be described in more detail. The scope of the present invention should not be limited by the descriptions below and may appropriately be modified and carried out apart from the following illustrative embodiments without departing from the spirit of the present invention.

The present invention relates to a method for producing carotenoids, including astaxanthin, by culturing a bacterium that concurrently produces astaxanthin and canthaxanthin (hereinafter occasionally referred to as a "carotenoid-producing bacterium" or "astaxanthin-producing bacterium") in a medium containing biotin (hereinafter referred to as "the method of the present invention"). According to the method of the present invention a ratio of concentration of produced canthaxanthin to concentration of produced astaxanthin in a culture product after the end of culture in the medium containing biotin is lower than that in a culture product obtained using a similar carotenoid-producing bacterium after the end of culture in a biotin-free medium. According to the method of the present invention, it becomes possible to produce astaxanthin of high concentration at low cost by adding biotin to a medium while suppressing the concentration of produced canthaxanthin.

A bacterium used in the method of the present invention is not limited as long as it concurrently produces astaxanthin and canthaxanthin. However, bacteria belonging to the genus *Paracoccus* are preferably used. Of the bacteria belonging to the genus *Paracoccus, Paracoccus carotinifaciens, Paracoccus marcusii,* and *Paracoccus haeundaensis* are preferably used, and *Paracoccus carotinifaciens* is particularly preferably used. Specific examples of bacterial strains belonging to the genus *Paracoccus* include *Paracoccus carotinifaciens* strain E-396 (FERM BP-4283) and *Paracoccus* bacterial strain A-581-1 (FERM BP-4671) (Patent Document 3 and Non-Patent Document 3). These bacterial strains also can be preferably used in the method of the present invention.

As a carotenoid-producing bacterium, a bacterium in which the nucleotide sequence of DNA corresponding to 16S ribosomal RNA is substantially homologous to the nucleotide sequence of E-396 shown in SEQ ID NO: 1 is preferably used. The phrase "substantially homologous" as used herein means that homology between nucleotide sequences is preferably 95% or more, more preferably 96% or more, further preferably 97% or more, particularly preferably 98% or more, and most preferably 99% or more in consideration of error frequency and the like in DNA sequencing. Homology can be determined using, for example, the Clustal W gene analysis software.

The phrase "the nucleotide sequence of DNA corresponding to 16S ribosomal RNA" means a nucleotide sequence obtained by substituting U (uracil) in the nucleotide sequence of 16S ribosomal RNA with T (thymine).

Classification of microorganisms based on the homology of the nucleotide sequence of 16S ribosomal RNA is recently becoming the mainstream. Since conventional classification of microorganisms is based on conventionally known mycological properties such as mobility, auxotrophy, and sugar utilization, microorganisms may incorrectly be classified when there happens a change in the characteristics due to spontaneous mutation or the like. On the other hand, the nucleotide sequence of 16S ribosomal RNA is fairly genetically stable, thereby classification based on homology thereof greatly improves reliability of the classification as compared to the conventional classification methods.

Homologies between the nucleotide sequence of 16S ribosomal RNA of *Paracoccus carotinifaciens* strain E-396 and the nucleotide sequences of 16S ribosomal RNAs of other carotenoid-producing bacteria i.e., *Paracoccus marcusii* strain DSM 11574 (International Journal of Systematic Bacteriology (1998), 48, 543-548), *Paracoccus* bacterial strain N-81106 (Patent Document 5), *Paracoccus haeundaensis* strain BC 74171 (Non Patent Document 4), *Paracoccus* bacterial strain A-581-1, and *Paracoccus* sp. strain PC-1 (Patent Document 6) are 99.7%, 99.7%, 99.6%, 99.4%, and 95.4%, respectively, showing that these strains are extremely close strains in terms of taxonomy. Accordingly, these strains may be regarded as making one group of carotenoid-producing bacteria. Thus, these bacterial strains may preferably be used in the method of the present invention for efficient production of astaxanthin.

According to the method of the present invention, mutant strains having improved astaxanthin productivity can also be used. Examples of such mutant strains include those disclosed in JP Patent Application Laid-open Publication No. 2001-95500 A and those disclosed in Patent Document 9.

Alternatively, mutant strains having improved astaxanthin productivity can be acquired by mutation treatment and screening. The method for mutation treatment is not particularly limited as long as it induces mutation. For example, chemical methods using a mutagen, such as N-methyl-N'-nitro-N-nitrosoguanidine (NTG) or ethyl methanesulfonate (EMS), physical methods, such as ultraviolet irradiation and X-ray irradiation, and biological methods, such as genetic recombination and transposon, can be used. In addition, mutant strains may be those obtained by naturally occurring mutation. In consideration of public acceptance or safety, it is preferable to use a microorganism that is not a genetically recombinant microorganism.

The method for screening for a mutant strain having improved astaxanthin productivity is not particularly limited, and may be, for example, a method in which a mutant strain of interest is selected according to the color tone of a colony on an agar medium, or a method in which mutant strains are cultured in a test tube, a flask, a fermenter, or the like and the mutant strain of interest is selected according to carotenoid pigment analysis utilizing absorbance, high-performance liquid chromatography, thin-layer chromatography, or the like.

The steps of mutation treatment and screening may be performed once or may be repeated twice or more such that for example, mutant strains are obtained by mutation treatment and screening and the obtained mutant strains are further subjected to another mutation treatment and screening to obtain a mutant strain having improved astaxanthin productivity.

In the method of the present invention, a mutant strain having lowered PHB (poly-β-hydroxybutyrate) producing ability may be used. For example, such a mutant strain can be induced from *Paracoccus* bacterial strain E-396 or A-581-1 described above or the like. It is known that astaxanthin-producing bacteria intracellularly accumulate PHB as a storage carbon source. Accumulation of FHB causes waste of the carbon source in a medium. Thus, it is preferable to minimize accumulation of PHB for production cost reduction. That is, it is effective to obtain a mutant strain characterized by accumulation of a small amount of PHB or no accumulation of PHB by performing mutation treatment and screening. A specific example of a method for obtaining a strain characterized by low PHB production is a method in which mutation treatment is performed in the manner described above, each mutant strain is cultured using a test tube, a flask, an agar medium, or the like, the amount of PHB is quantified, and a mutant strain characterized by low PHB production is selected.

In the method of the present invention, a mutant strain having lowered gluconic acid producing ability may also be used. For example, such a mutant strain can be induced from *Paracoccus* bacterial strain E-396 or A-581-1 described above or the like. Production of gluconic acid results in waste of the carbon source in a medium corresponding to the produced gluconic acid. In addition, accumulation of a large amount of gluconic acid causes inhibition of bacterial growth or carotenoid production. Thus, it is effective to in gluconic acid production for carotenoid production. A specific example of a method for obtaining a strain characterized by low gluconic acid production is a method in which mutation treatment is performed in the manner described above, each mutant strain is cultured in a test tube, a flask, or the like, the pH of each resulting culture liquid is measured to select mutant strains for which a small decrease in the pH of the culture liquid has been confirmed, and then the amount of gluconic acid in the culture liquid of each selected mutant strain is quantified to select a mutant strain characterized by low gluconic acid production.

Mutant strains to which preferable properties have been imparted, such as the mutant strain having improved astaxanthin productivity, the mutant strain having lowered PHB producing ability, and the mutant strain having lowered gluconic acid producing ability described above, may be separately obtained. Alternatively, mutation treatment and screening can be repeated in order to obtain a mutant strain having two or more such properties. It is also possible to obtain a mutant strain to which two or more properties have been simultaneously imparted by carrying out a combination of two or in ore types of screening methods with a single mutation treatment. A mutant strain having two or more preferable properties may also be used in the method of the present invention.

Strain E-396 exemplified as a carotenoid-producing bacterium used in the method of the present invention has been deposited as international deposition with the International Patent Organism Depositary (IPOD) the National institute of Advanced Industrial Science and Technology (AIST) as described below.
International Depositary Authority:
  The International Patent Organism Depositary (IPOD), the National Institute of Advanced Industrial Science and Technology (AIST) (the former National Institute of Bioscience and Human-Technology, the Agency of Industrial Science and Technology, the Ministry of International Trade and Industry)
  Tsukuba Central 6, 1-1-1 Higashi, Tsukuba, Ibaraki, 305-8566, Japan
Identification Indication: E-396
Accession No.: PERM BP-4283
Date of the original deposit: Apr. 27, 1993

Strain A-581-1 exemplified as another carotenoid-producing bacterium used in the method of the present invention has been deposited as international deposition with the above authority as described below.
Identification indication: A-581-1
Accession No.: FERM BP-4671
Date of the original deposit: May 20, 1994

Examples of carotenoids other than astaxanthin and canthaxanthin produced by the method of the present invention include, but are not particularly limited to, adonixanthin, phoenicoxanthin, β-carotene, echinenone, asteroidenone, 3-hydroxyechinenone, zeaxanthin, β-cryptoxanthin, and lycopene. Preferable examples include adonixanthin and adonirubin. One type of carotenoid or a combination of multiple types of carotenoids may be produced according to the method of the present invention.

Hereinafter, a method for culturing the above-described bacteria in the method of the present invention will be described. The term "culture product" used herein is not limited to a culture liquid and thus it may contain a solid, a semi-solid, or the like.

A medium for producing astaxanthin used for culture in the method of the present invention may be any medium as long as it contains biotin and it allows the growth of an astaxanthin-producing bacterium and the production of astaxanthin. Preferably, a medium containing a carbon source, a nitrogen source, an inorganic salt, and if necessary, a vitamin or the like is used. That is, biotin is added to a medium that allows the growth of an astaxanthin-producing bacterium and the production of astaxanthin according to the method of the present invention.

Examples of carbon sources include: sugars such as glucose, sucrose, lactose, fructose, trehalose, mannose, mannitol, and maltose; organic acids such as acetic acid, fumaric acid, citric acid, propionic acid, malic acid, malonic acid, and pyruvic acid; alcohols such as ethanol, propanol, butanol, pentanol, hexanol, isobutanol and glycerol; and oils and fats such as soybean oil, rice bran oil, olive oil, corn oil, sesame oil, and linseed oil, among which glucose or sucrose is preferably used. One or more types of these carbon sources can be used. The amount of a carbon source added to a preculture medium (starting medium) differs depending on the type of the carbon source, and may adequately be adjusted, but it is usually 1 to 100 g and preferably 2 to 50 g per 1 L of medium. The carbon source can be added not only to the starting medium but it may also preferably be additionally supplied during culture in a sequential or continuous manner.

Examples of inorganic nitrogen sources include: ammonium salts such as ammonium nitrate, ammonium sulfate, ammonium chloride, and ammonium phosphate; nitrates such as potassium nitrate; ammonia; and urea. One or more types of these inorganic nitrogen sources are used. The amount of an added differs depending on the type of the nitrogen source and may appropriately be adjusted, but it is usually 0.1 g to 20 g and preferably 0.2 to 10 g per 1 L of the medium.

Examples of organic nitrogen sources include corn steep liquor (including filtrated products), pharmamedia, soybean meal, soybean flour, peanut meal, monosodium glutamate, Distillers' solubles and dried yeast. Among them, one or more types of organic nitrogen sources are used. The concentration of an organic nitrogen source added differs depending on the type of the nitrogen source and may appropriately be adjusted, but it is usually 0 to 80 g/L, and preferably 0 to 30 g/L, in the medium.

The inorganic nitrogen source and the organic nitrogen source are usually added to the starting medium; however, they may also preferably be additionally supplied in a sequential or continuous manner.

Examples of inorganic salts include: phosphates such as potassium dihydrogen phosphate, dipotassium hydrogen phosphate, and disodium hydrogen phosphate; magnesium salts such as magnesium sulfate and magnesium chloride;

iron salts such as iron sulfate and iron chloride; calcium salts such as calcium chloride and calcium carbonate; sodium salts such as sodium carbonate and sodium chloride; manganese salts such as manganese sulfate; cobalt salts such as cobalt chloride; copper salts such as copper sulfate; zinc salts such as zinc sulfate; molybdenum salts such as sodium molybdate; nickel salts such as nickel sulfate; selenium salts such as sodium selenate; boric acid; and potassium iodide. One or more types or these inorganic salts are used. The amount of an inorganic salt added differs depending on the type of the inorganic salt and may appropriately be adjusted, but it is usually 0.0001 to 15 g per 1 L of the medium. The concentration of a phosphate, a magnesium salt, a calcium salt, a sodium salt, or an iron salt is preferably 0.02 to 15 g/L in the medium. When a manganese salt, a cobalt salt, a copper salt, a zinc salt, a molybdenum salt, a nickel salt, a selenium salt, boric acid, potassium iodide, or the like is added, the concentration thereof is preferably 0.1 to 15 mg/L. The inorganic salt is usually added to the starting medium; however, it may also be additionally supplied in a sequential or continuous manner.

Examples of vitamins other than biotin which can be used include cyanocobalamin, riboflavin pantothenic acid, pyridoxine, thiamine, ascorbic acid, folic acid, niacin, p-aminobenzoic acid, inositol, and choline. The proportion of a vitamin added differs depending on the type of the vitamin and may appropriately be adjusted, but it is usually 0.001 to 1000 mg and preferably 0.01 to 100 mg per 1 L of the medium. The vitamin is usually added to the starting medium; however, it may additionally be added in a sequential or continuous manner.

The method of the present invention has a feature of culturing an astaxanthin-producing bacterium in a medium to which biotin has been added. Astaxanthin of high concentration can be produced while keeping canthaxanthin concentration at a low level by culturing an astaxanthin-producing bacterium in a medium to which biotin has been added.

Biotin used in the method of the present invention may be DL-biotin or D-biotin. D-biotin is preferably used. Biotin is usually added to the starting medium; however, biotin may be added intermittently or continuously during culture. Alternatively, biotin may be added to the starting medium and further added intermittently or continuously during culture. Biotin may be mixed with a basal medium and then the medium may be sterilized. Alternatively, biotin may separately be sterilized and then added to a basal medium. The method for sterilizing biotin is not particularly limited and may be heat sterilization or filtration sterilization.

The lower limit of the concentration of biotin added to the medium is not particularly limited, but is preferably 0.001 mg/L, more preferably 0.005 mg/L, further preferably 0.01 mg/L, and particularly preferably 0.02 mg/L. The upper limit of the concentration of biotin added is not particularly limited, but is preferably 50 mg/L, more preferably 20 mg/L, further preferably 10 mg/L, particularly preferably 5 mg/L, and most preferably 2 mg/L.

An antifoamer is preferably used in the method of the present invention in order to prevent formation of bubbles in the culture product. Any type of antifoamer can be used as long as it can prevent generation of bubbles or remove the generated bubbles with less inhibition effect on the astaxanthin-producing bacterium. Examples of the antifoamer include alcohol-based antifoamers, polyether-based antifoamers, ester-based antifoamers, fatty acid-based antifoamers, silicone-based antifoamers, and sulfonic acid-based antifoamers. The amount of an antifoamer added differs depending on the type of the antifoamer and may appropriately be adjusted, but it is usually 0.01 g to 10 g per 1 L of the medium.

The antifoamer is usually added to the starting medium prior to sterilization. It may also be additionally supplied during culture in a continuous or intermittent manner. Examples of a method for adding an antifoamer during culture include: a method in which bubbles are detected using a sensor so as to automatically add an antifoamer; a method in which an antifoamer is added at constant time intervals using a program timer; and a method in which an antifoamer is mixed with a carbon source, a nitrogen source, a pH adjuster, or the like for feeding such that the mixture is added in response to changes in the growth rate. The antifoamer added to the starting medium may be the same as that added to a culture product during culture. Alternatively, different types of antifoamers can be used by making use of the effects thereof.

According to the method of the present invention, pH of the medium at the initiation of culture is adjusted to 2 to 12, preferably 6 to 9, and more preferably 6.5 to 8.0. Preferably, pH within this range is maintained during culture. A preferable method for maintaining pH is a method in which pH of a culture liquid is measured online using a pH electrode provided inside a fermenter to automatically supply alkali. Examples of pH adjusters include an aqueous sodium hydroxide solution, an aqueous potassium hydroxide solution, an aqueous sodium carbonate solution, ammonia water, ammonia gas, an aqueous sulfuric acid solution, and a mixture thereof.

A medium used in the method of the present invention is sterilized before being used for culturing a bacterium. Sterilization can appropriately be carried out by those skilled in the art. For example, the medium in a suitable container can be subjected to heat sterilization in an autoclave. Alternatively, filtration sterilization may be carried out using a sterilizing filter. In another case, sterilization may be carried out by jacket heating and steam injection. If a carbon source such as glucose is subjected to heat sterilization with other medium components, it turns brownish and thus it may be separately sterilized. A vitamin or a minute amount of metal may be subjected to heat sterilization with a basal medium or it may be separately sterilized in order to prevent deactivation or precipitation.

According to the method of the present invention, an astaxanthin-producing bacterium is inoculated into the medium containing biotin prepared as described above and cultured under predetermined conditions. Inoculation is carried out by appropriately growing the bacterial strain by seed culture using a test tube, a flask, a fermenter, or the like, and adding the resulting culture product to the medium containing biotin for producing astaxanthin. The medium used for seed culture is not particularly limited and thus it may be a medium containing biotin or a biotin-free medium as long as it provides good growth of the astaxanthin-producing bacterium.

Culture is carried out in a suitable culture container. The culture container can appropriately be selected according to the culture volume, including, for example, a test tube, a flask, a fermenter, or the like.

The temperature for culture is, for example, 15° C. to 40° C., preferably 20° C. to 35° C., and more preferably 25° C. to 32° C. Culture is carried out under aerobic conditions within a culture period of generally 1 day to 20 days, preferably 2 to 12 days, more preferably 3 to 9 days, and particularly preferably 4 to 7 days.

Examples of aerobic conditions include shaking culture or aeration/agitation culture. Lack of oxygen would negatively influence the growth of the astaxanthin-producing bacterium or the production of the carotenoid. Thus, continuous monitoring of the dissolved oxygen concentration is preferably carried out using a dissolved oxygen electrode.

The number of microorganisms is low immediately after the initiation of culture, and thus the dissolved oxygen concentration is close to the saturation concentration. However, as microorganisms grow and thus the oxygen consumption increases, the dissolved oxygen concentration gradually decreases. Culture phases can be defined as follows: a period between the initiation of culture and when the dissolved oxygen concentration has decreased to a certain level, for example, 0 to 5 ppm, and preferably 1 to 4 ppm, which corresponds to the initial culture phase; a period between the end of the initial culture phase and when the concentration of produced astaxanthin has reached the maximum level, which corresponds to the intermediate phase of culture; and a period between when the concentration of produced astaxanthin has reached the maximum level and the end of culture, which corresponds to the terminal phase of culture.

In order to allow the dissolved oxygen concentration to fall within the control region at the earliest possible time, the aeration volume, the number of agitation rotations, and pressure may be set at low levels in the initial phase of culture. Note that it is necessary to achieve the minimum necessary number of agitation rotations in order to maintain the favorable state of mixings of a culture product. It is also necessary to achieve pressurization at the minimum necessary level in order to prevent germ contamination.

Oxygen consumption by the microorganism becomes most active in the intermediate phase of culture. Here, if aeration agitation is insufficient, the dissolved oxygen concentration decreases to zero, that is to say, oxygen depletion occurs. This negatively influences the growth of the microorganism or the production of the carotenoid. Thus, it is preferable to control the dissolved oxygen concentration to prevent oxygen depletion in the intermediate phase of culture. The dissolved oxygen concentration can be controlled by, for example, changing the number of agitation rotations, the aeration volume, internal pressure, the oxygen concentration in an aeration gas.

According to the method of the present invention, the higher the dissolved oxygen concentration in a culture product is during culture of an astaxanthin-producing bacterium, the lower a ratio of concentration of produced canthaxanthin to concentration of produced astaxanthin tends to be. Thus, the dissolved oxygen concentration in the culture product in the intermediate phase of culture is controlled preferably at 1 ppm or more, more preferably at 1.5 ppm or more, further preferably at 2 ppm or more and particularly preferably at 2.5 ppm or more. The upper limit of the dissolved oxygen concentration in the culture product in the intermediate phase of culture that falls within the controlled range is not particularly limited, but is preferably 8 ppm, more preferably 7 ppm, further preferably 6 ppm, and particularly preferably 5 ppm.

Although the dissolved oxygen concentration in the culture product in the intermediate phase of culture may be controlled at a given level, it is also effective to increase the dissolved oxygen concentration in a stepwise or continuous manner in order to achieve high levels of the astaxanthin concentration while suppressing the canthaxanthin concentration in the culture product. The number of steps to increase the dissolved oxygen concentration is not particularly limited as long as it is at least one step. For example, the dissolved oxygen concentration can be increased semi-continuously or continuously by 0.2 ppm per hour for 20 hours. The lower limit of the dissolved oxygen concentration prior to the stepwise or continuous increase of the dissolved oxygen concentration in the culture product (i.e., the initial dissolved oxygen concentration) is not limited, but is preferably 1 ppm, more preferably 1.5 ppm, and further preferably 2 ppm. The upper limit of the same is also not limited, but is preferably 3.5 ppm, more preferably 3 ppm, and further preferably 2.5 ppm. The lower limit or the dissolved oxygen concentration following the stepwise or continuous increase of the dissolved oxygen concentration in the culture product is not limited, but is preferably 2.5 ppm, more preferably 3 ppm, and further preferably 3.5 ppm. The upper limit of the same is also not limited, but is preferably 8 ppm, more preferably 7 ppm, further preferably 6 ppm, and particularly preferably 5 ppm.

The timing at which the dissolved oxygen concentration in the culture product in the intermediate phase of culture starts to be increased in a stepwise or continuous manner is not particularly limited, but is preferably 0 to 60 hours, more preferably 2 to 50 hours, further preferably 4 to 40 hours, and particularly preferably 6 to 30 hours from the beginning of the intermediate phase of culture. The time during which the dissolved oxygen concentration in a culture product starts to be increased in a stepwise or continuous manner so as to achieve the highest dissolved oxygen concentration is not limited. When the dissolved oxygen concentration is shifted by a single step, the highest dissolved oxygen concentration may be achieved within 1 hour. When the dissolved oxygen concentration is increased semi-continuously or continuously by 2 or more steps, the time during which the dissolved oxygen concentration in the culture product starts to be increased so as to achieve the highest dissolved oxygen concentration is not limited. In this case, however, that time is preferably 2 to 120 hours, more preferably 4 to 100 hours, further preferably 6 to 90 hours, particularly preferably 8 to 80 hours, and most preferably 10 to 70 hours.

The dissolved oxygen concentration in the culture product can be preferably increased or decreased during culture while carrying out sampling of the culture product as needed and analyzing the carotenoid composition in the intermediate phase of culture so as to adjust the ratio of canthaxanthin concentration to astaxanthin concentration to a desired level. Specifically, it is effective to raise the controlling level of the dissolved oxygen concentration in the culture product when the ratio of canthaxanthin concentration to astaxanthin concentration is higher than the desired level, while it is effective to lower the dissolved oxygen concentration in the culture product when the ratio of canthaxanthin concentration to astaxanthin concentration is lower than the same.

In the terminal phase of culture, the microorganism has a reduced level of the activity of consuming oxygen, resulting in termination of the growth of the bacterium and the production of the carotenoid. Accordingly, there is no need to control the dissolved oxygen concentration in the culture product as strictly as in the intermediate phase of culture. However, it is possible to continuously control the dissolved oxygen concentration at the same level in the late period of the intermediate phase of culture or to carry out culture by agitation at a constant rate with a constant aeration volume.

The ratio of canthaxanthin concentration to astaxanthin concentration in the culture product obtained as a final product after the end of culture by the above method is preferably 25% by mass or less, more preferably 20% by mass or less, further preferably 15% by mass or less, even further preferably 8% by mass or less, particularly preferably 6% by mass or less, and most preferably 4% by mass or less. The lower limit of the ratio of canthaxanthin concentration to astaxanthin concentration in the culture product after the end of culture is not particularly limited, but is preferably 0.5% by mass and more preferably 1.0% by mass. The culture product after the end of culture in which the ratio of canthaxanthin concentration to astaxanthin concentration is 25% by mass or less can be preferably used for feed additives. In addition, the culture product in which the same is 8% by mass or less can be preferably used for food.

A bacterium that concurrently produces astaxanthin and canthaxanthin also produces, as a by-product, adonixanthin at the same time. A ratio of adonixanthin concentration to astaxanthin concentration in the culture product after the end of culture obtained by culture according to the above method is preferably 100% by mass or less, more preferably 90% by mass or less, further preferably 80% by mass or less, even further preferably 30% by mass or less, particularly preferably 25% by mass or less, and most preferably 20% by mass or less. The lower limit of the ratio of adonixanthin concentration to astaxanthin concentration in the culture product after the end of culture is not particularly limited, but is preferably 1% by mass and more preferably 5% by mass.

A bacterium used in the method of the present invention produces gluconic acid in the culture liquid. When gluconic acid is produced, it causes waste of the carbon source in a medium corresponding to the produced gluconic acid. When a large amount of gluconic acid accumulates, inhibition of bacterial growth or carotenoid production occurs. Accordingly, it is effective to minimize gluconic acid production for carotenoid production. According to the method of the present invention, the amount of produced gluconic acid can be reduced by adding biotin to a medium. The gluconic acid concentration in the culture product obtained as a final product after the end of culture is preferably 30 g/L or less, more preferably 20 g/L or less, further preferably 10 g/L or less, and particularly preferably 5 g/L or less. The lower limit thereof is 0 g/L.

According to the method of the present invention, production of PHB (poly-β-hydroxybutyrate) can be inhibited by adding biotin to the medium. A PHB content in the culture product obtained as a final product after the end of culture based on dry cells is preferably 30% by mass or less, more preferably 20% by mass or less, further preferably 10% by mass or less, and particularly preferably 5% by mass or less. The lower limit thereof is 0% by mass. In particular, the culture product in which the PHB content in the culture product after the end of culture based on dry cells is 30% by mass or less can be preferably used as a feed additive.

In the method of the present invention, a carotenoid in a culture product obtained by culturing an astaxanthin-producing bacterium or a carotenoid collected from a culture product can be quantified by, for example, high performance liquid chromatography.

As described above, the culture product obtained by culturing an astaxanthin-producing bacterium may be directly used as a carotenoid. Alternatively, a culture supernatant, a cell concentrate (cell concentrate liquid), wet cells, dry cells, cell lysate, and the like are prepared from the culture product such as a culture liquid, and they can be used as preparations. Further, a carotenoid can be obtained from such culture product or preparation by extraction, purification, or the like.

The culture supernatant can be prepared by subjecting the culture product to centrifugation or filtration so as to remove bacterial cells from the culture product. The cell concentrate (the cell concentrate liquid) can be obtained by subjecting, the culture product to centrifugation, membrane filtration concentration, or decantation. The wet cells can be obtained by subjecting the culture product to centrifugation or filtration. The dry cells can be obtained by drying the culture product, the wet cells or the cell concentrate (the cell concentrate liquid) by a general method for drying. The dry cells containing a carotenoid obtained in such manner can be directly used as a feed additive.

A method for collecting a carotenoid from the above culture product or preparation is not particularly limited in the method of the present invention. The method may be any method that allows efficient and stable collection of the carotenoid. Those skilled in the art can carry out such a method by selecting an adequate technique from among known extraction and purification techniques.

In addition, prior to extraction, the culture product or preparation may be subjected to at least one treatment selected from among chemical treatment using an alkaline reagent or a surfactant, biochemical treatment using a lytic enzyme, a lipid-degrading enzyme, a protease, or the like, and physical treatment such as ultrasonication or pulverization.

For instance, if the carotenoid is extracted from the culture product or preparation, solvents used for extraction and washing are not particularly limited. However, examples thereof include lower alcohols (e.g., methanol, ethanol, and isopropanol), acetone, tetrahydrofuran, methyl ethyl ketone, methyl isobutyl ketone, dichloromethane, chloroform, dimethylformamide, and dimethylsulphoxide.

If it is desired to minimize the risk of oxidation of the carotenoid during the extraction operation, extraction can be carried out under an inert gas atmosphere such as a nitrogen gas atmosphere. It is also possible to select an antioxidant used for pharmaceutical agents or foods and add it to the extraction solvent according to need. Alternatively, a combination of such treatments may be carried out.

In addition, extraction may be carried out under conditions comprising shielding light in order to minimize the risk of degradation of the carotenoid due to light.

The thus obtained extract can be directly used as a carotenoid and may be further purified before use.

A method for separating the bacterium and the like from the extract (e.g., the liquid extract) obtained after the extraction operation is not particularly limited. However, examples thereof include membrane filtration, centrifugation, and decantation.

In general, heating and/or vacuum concentration, crystallization, or the like can be used as a method for obtaining a carotenoid precipitate from the extract. In addition to such method, a carotenoid pigment may be separated by low-temperature precipitation or precipitation using an acid/alkali agent or a different salt without concentration. For industrial use, the extract is desirably subjected to crystallization.

If necessary, the resulting carotenoid precipitate may be subjected to suspension/agitation for washing using a small amount of a solvent such as lower alcohol.

A washing means is not particularly limited, while practically preferable methods include a method in which filtration is performed following suspension/agitation and a method in which a liquid is passed through from above a precipitate.

The culture product, preparation, extract, or purified product obtained in the above manner may be used alone as a carotenoid or may be mixed and used at given proportions.

EXAMPLES

Hereinafter, the present invention will be described specifically by way of examples, although the scope of the present invention should not be limited to the following examples.

Carotenoids were quantified in the examples as described below using high performance liquid chromatography (HPLC).

Two columns (Inertsil SIL-100A, 5 μm (φ: 4.6×250 mm) (GL Sciences)) were used in tandem. Elution was performed by running an n-hexane/tetrahydrofuran/methanol mixture liquid (40:20:1) as a mobile phase at a rate of 1.0 mL per minute at a constant temperature around room temperature. For measurement, samples dissolved in tetrahydrofuran were 100-fold diluted with the mobile phase and 20 μL of the resultant was injected. The column eluent was detected at a wavelength of 470 nm. Furthermore, astaxanthin (produced by Sigma) (Cat. No. A9335) was used as a standard preparation for quantification. The concentration of astaxanthin in the standard solution was determined according to the following formula after measuring: (A): the absorbance of the standard solution at 477 nm and; (B): the area percentage (%) of the astaxanthin peak obtained upon HPLC analysis under the above conditions.

Concentration of astaxanthin (mg/L)=$A/2150 \times B \times 100$

Example 1

A hundred milliliter of a medium (having the following composition: sucrose: 30 g/L; corn steep liquor: 30 g/L; potassium dihydrogen phosphate: 1.5 g/L; disodium hydrogen phosphate dodecahydrate: 3.8 g/L; calcium chloride dihydrate: 5.0 g/L; magnesium sulfate heptahydrate: 0.7 g/L; and iron sulfate heptahydrate: 0.3 g/L (pH 7.2)) was poured into a 500-ml cotton-plugged conical flask and sterilized in an autoclave at 121° C. for 15 minutes to prepare seven flasks containing medium for seeding.

Next, 2.0 L of a medium (having the following composition glucose: 20 g/L; corn steep liquor: 30 g/L; ammonium sulfate: 0.5 g/L; potassium dihydrogen phosphate: 2.25 g/L; disodium hydrogen phosphate dodecahydrate: 5.7 g/L; calcium chloride dihydrate: 0.1 g/L; magnesium sulfate heptahydrate: 0.5 g/L; iron sulfate heptahydrate: 5 g/L; and an alcohol-based antifoamer: 0.5 g/L) was poured into a 5-L fermenter. Seven fermenters were prepared in such manner. D-biotin was added to the fermenters to result in concentrations of 0, 0.001, 0.01, 0.1, 1.0, 10, and 50 mg/L, respectively, and each resultant was sterilized in an autoclave at 121° C. for 30 minutes.

A platinum loopful of *Paracoccus carotinifaciens* strain E-396 (FERM BP-4283) was inoculated into the medium for seeding in each flask prepared above, followed by rotary shaking culture at 100 rpm and 28° C. for 2 days. Subsequently, the resulting culture liquids (80 mL each) were separately introduced into the fermenters for aerobic culture at 28° C. with an aeration volume of 1 vvm for 120 hours. pH was continuously controlled with 15% ammonia water so as to be maintained at 7.2 during culture. Glucose (30 g) was added on the 1st, 2nd, 3rd, and 4th days of culture to prevent depletion of glucose. In addition, the number of agitation rotations was changed (the lowest number of agitation rotations: 200 rpm) to maintain the dissolved oxygen concentration in each culture liquid at 2 ppm in the intermediate phase of culture. Once bubble formation was detected with a bubble sensor, an alcohol-based antifoamer was automatically added to prevent bubble formation.

The carotenoid concentration, the gluconic acid concentration, and the PHB content based on dry cells in each culture liquid at the end of culture were determined. Table 1 shows the results. It was found that the ratio of concentration of canthaxanthin to concentration of astaxanthin was lower in each experimental plot to which biotin had been added at 0.001 to 50 mg/L than that in a plot to which no biotin had been added.

TABLE 1

| Biotin concentration mg/L | 0 | 0.001 | 0.01 | 0.1 | 1 | 10 | 50 |
|---|---|---|---|---|---|---|---|
| Canthaxanthin mg/L | 5.2 | 3.9 | 3.3 | 3.3 | 3.0 | 2.7 | 2.5 |
| Astaxanthin mg/L | 15.2 | 15.7 | 16.5 | 17.0 | 15.9 | 14.3 | 14.1 |
| Adonixanthin mg/L | 6.3 | 6.6 | 6.7 | 6.9 | 6.8 | 7.3 | 7.2 |
| Canthaxanthin/Astaxanthin mass % | 34.2 | 24.8 | 20.0 | 19.4 | 18.9 | 18.9 | 17.7 |
| Adonixanthin/Astaxanthin mass % | 41.4 | 42.0 | 40.6 | 40.6 | 42.8 | 51.0 | 51.1 |
| Gluconic acid g/L | 45 | 23 | 19 | 14 | 13 | 13 | 10 |
| PHB mass % | 35 | 29 | 24 | 25 | 22 | 21 | 23 |

Example 2

A hundred milliliter of a medium (having the following composition: sucrose: 30 g/L; corn steep liquor; 30 g/L; potassium dihydrogen phosphate: 1.5 g/L; disodium hydrogen phosphate dodecahydrate: 3.8 g/L; calcium chloride dihydrate: 5.0 g/L; magnesium sulfate heptahydrate: 0.7 g/L; and iron sulfate heptahydrate: 0.3 g/L (pH 7.2)) was poured into a 500-ml cotton-plugged conical flask and sterilized in an autoclave at 121° C. for 20 minutes to prepare eight flasks containing medium for seeding.

Next, 2.0 L of a medium (having the following composition: sucrose: 40 g/L; corn steep liquor: 30 g/L; ammonium sulfate: 0.5 g/L; potassium dihydrogen phosphate: 2.25 g/L; disodium hydrogen phosphate dodecahydrate: 5.7 g/L; calcium chloride dihydrate: 0.1 g/L; magnesium sulfate heptahydrate: 0.5 g/L; iron sulfate heptahydrate: 5 g/L; and an alcohol-based antifoamer: 0.5 g/L) was poured into a 5-L fermenter. Eight tanks were prepared in such manner. D-biotin was added to each fermenter to result in 0.1 mg/L, and each resultant was sterilized in an autoclave at 121° C. for 30 minutes.

A platinum loopful of *Paracoccus carotinifaciens* strain E-396 (FERM BP-4283) was inoculated into the medium for seeding in each flask prepared above, followed by rotary shaking culture at 100 rpm and 28° C. for 2 days. Subsequently, the resulting culture liquids (80 mL each) were separately introduced into the fermenters for aerobic culture at 28° C. with an aeration volume of 1 vvm for 120 hours. pH was continuously controlled with 15% ammonia water so as to be maintained at 7.2 during culture. Sucrose (30 g) was added on the 1st, 2nd, 3rd, and 4th days of culture to prevent depletion of sucrose. In addition, the number of agitation rotations was changed (the lowest number of agitation rotations: 200 rpm) to maintain the dissolved oxygen concentrations in the culture liquids at 0.5, 1, 2, 3, 4, 5, 6, and 7 ppm in the intermediate phase of culture. Once hobble formation was detected with a bubble sensor, an alcohol-based antifoamer was automatically added to prevent bubble formation.

The carotenoid concentration, the gluconic acid concentration, and the PHB content based on dry cells in each culture liquid at the end of culture were determined. Table 2 shows the results. It was found that the ratio of canthaxanthin concentration to astaxanthin concentration tended to decrease as the dissolved oxygen concentration was increased, and that the ratio can be reduced to 1.4%.

For comparison, a similar experiment was performed using a biotin-free medium. Table 3 shows the results. The ratio of canthaxanthin concentration to astaxanthin concentration was able to be reduced to 9% at most.

Next, 2.0 L of a medium (having the following composition: glucose: 30 g/L; corn steep liquor: 30 g/L; ammonium sulfate: 0.5 g/L; potassium dihydrogen phosphate: 2.25 g/L; disodium hydrogen phosphate dodecahydrate: 5.7 g/L; calcium chloride dihydrate: 0.1 g/L; magnesium sulfate heptahydrate: 0.5 g/L; iron sulfate heptahydrate: 5 L-monosodium glutamate monohydrate: 6 g/L; and an alcohol-based antifoamer: 0.5 g/L) was poured to a 5-L fermenter. Eight fermenters were prepared in such manner. D-biotin was added to each fermenter to result in 0.1 mg/L, and each resultant was sterilized in an autoclave at 121° C. for 30 minutes.

A platinum loopful of *Paracoccus* bacterial strain LP-26 selected above was inoculated into the medium for seeding in the flask as described above, followed by rotary shaking culture at 100 rpm and 28° C. for 2 days. The resulting culture liquids (80 mL each) were separately introduced into the fermenters for aerobic culture at 28° C. with an aeration volume of 1 vvm for 140 hours. The pH was continuously

TABLE 2

Addition of 0.1 mg/L biotin

| Dissolved oxygen concentration ppm | 0.5 | 1 | 2 | 3 | 4 | 5 | 6 | 7 |
|---|---|---|---|---|---|---|---|---|
| Canthaxanthin mg/L | 7.3 | 3.3 | 1.6 | 1.2 | 0.6 | 0.3 | 0.2 | 0.1 |
| Astaxanthin mg/L | 8.3 | 13.3 | 20.2 | 20.9 | 15.8 | 11.3 | 9.6 | 7.0 |
| Adonixanthin mg/L | 1.4 | 2.3 | 3.9 | 5.1 | 6.1 | 8.2 | 8.8 | 11.4 |
| Canthaxanthin/Astaxanthin mass % | 88.0 | 24.8 | 7.9 | 5.7 | 3.8 | 2.7 | 2.1 | 1.4 |
| Adonixanthin/Astaxanthin mass % | 16.9 | 17.3 | 19.3 | 24.4 | 38.6 | 72.6 | 91.7 | 163 |
| Gluconic acid g/L | 24 | 19 | 17 | 14 | 16 | 11 | 10 | 9 |
| PHB mass % | 25 | 19 | 18 | 17 | 14 | 20 | 13 | 17 |

TABLE 3

Without addition of biotin

| Dissolved oxygen concentration ppm | 0.5 | 1 | 2 | 3 | 4 | 5 | 6 | 7 |
|---|---|---|---|---|---|---|---|---|
| Canthaxanthin mg/L | 6.7 | 4.1 | 3.2 | 2.2 | 1.2 | 0.7 | 0.5 | 0.4 |
| Astaxanthin mg/L | 3.0 | 7.8 | 12.3 | 13.3 | 10.9 | 7.8 | 5.5 | 4.2 |
| Adonixanthin mg/L | 0.6 | 1.7 | 3.4 | 5.5 | 6.8 | 6.5 | 7.3 | 8.7 |
| Canthaxanthin/Astaxanthin mass % | 223 | 52.6 | 26.0 | 16.5 | 11.0 | 90 | 9.1 | 9.5 |
| Adonixanthin/Astaxanthin mass % | 20.0 | 21.8 | 27.6 | 41.4 | 62.4 | 83.3 | 133 | 207 |
| Gluconic acid g/L | 56 | 47 | 33 | 44 | 35 | 36 | 31 | 31 |
| PHB mass % | 44 | 47 | 29 | 34 | 27 | 27 | 36 | 32 |

Example 3

*Paracoccus carotinifaciens* strain E-396 (FERM BP-4283) was subjected to mutation treatment with N-methyl-N'-nitro-N-nitrosoguanidine, and a colony taking on a strong red color was selected. The PHB concentration and the carotenoid concentration in the culture liquid of the selected strain were determined, and the LP-26 mutant strain having low PHB producing ability and high astaxanthin producing ability was selected.

A hundred milliliter of a medium (having the following composition: sucrose: 30 g/L; corn steep liquor: 30 g/L; potassium dihydrogen phosphate: 1.5 g/L; disodium hydrogen phosphate dodecahydrate: 3.8 g/L; calcium chloride dihydrate: 5.0 g/L; magnesium sulfate heptahydrate: 0.7 g/L; and iron sulfate heptahydrate: 0.3 g/L; (pH 7.2)) was poured into a 500-ml cotton-plugged conical flask and sterilized in an autoclave at 121° C. for 20 minutes to prepare a flask containing the medium for seeding.

controlled with 15% ammonia water so as to be maintained at 7.2 during culture. Glucose (50 g) was added on the 1st 2nd, 3rd, and 4th days of culture to prevent depletion of glucose. In addition, the number of agitation rotations was changed (the lowest number of agitation rotations: 100 rpm) to maintain the dissolved oxygen concentrations in the culture liquids at 0.5, 1, 2, 3, 4, 5, 6, and 7 ppm in the intermediate phase of culture. Once bubble formation was detected with a bubble sensor, an alcohol-based antifoamer was automatically added to prevent bubble formation.

The carotenoid concentration, the gluconic acid concentration, and the PHB content based on dry cells in each culture liquid at the end of culture were determined. Table 4 shows the results. It was found that the ratio of canthaxanthin concentration to astaxanthin concentration tended to decrease as the dissolved oxygen concentration was increased, and that the ratio can be reduced to 1.6%.

For comparison, a similar experiment was performed using a biotin-free medium while controlling the dissolved oxygen concentration at 2 ppm in the intermediate phase or culture. Table 5 shows the results. The ratio of canthaxanthin concentration to astaxanthin concentration was 8% in the medium to which biotin had been added while controlling the dissolved oxygen concentration at 2 ppm. On the other hand, it was as high as 26.8% in the biotin-free medium.

TABLE 4

Addition of 0.1 mg/L biotin

| Dissolved oxygen concentration ppm | 0.5 | 1 | 2 | 3 | 4 | 5 | 6 | 7 |
|---|---|---|---|---|---|---|---|---|
| Canthaxanthin mg/L | 243 | 122 | 59 | 52 | 24 | 10 | 6 | 4 |
| Astaxanthin mg/L | 301 | 499 | 741 | 746 | 577 | 401 | 315 | 244 |
| Adonixanthin mg/L | 45 | 73 | 130 | 201 | 255 | 259 | 309 | 332 |
| Canthaxanthin/Astaxanthin mass % | 80.7 | 24.4 | 8.0 | 7.0 | 4.2 | 2.5 | 1.9 | 1.6 |
| Adonixanthin/Astaxanthin mass % | 15.0 | 14.6 | 17.5 | 26.9 | 44.2 | 64.6 | 98.1 | 136 |
| Gluconic acid g/L | 26 | 17 | 19 | 15 | 15 | 16 | 14 | 10 |
| PHB mass % | 12 | 10 | 9 | 6 | 1 | 3 | 0 | 6 |

TABLE 5

Without addition of biotin

| | Dissolved oxygen concentration ppm 2 |
|---|---|
| Canthaxanthin mg/L | 132 |
| Astaxanthin mg/L | 493 |
| Adonixanthin mg/L | 144 |
| Canthaxanthin/Astaxanthin mass % | 26.8 |
| Adonixanthin/Astaxanthin mass % | 29.2 |
| Gluconic acid g/L | 35 |
| PHB mass % | 22 |

Next, experiments for shifting the dissolved oxygen concentration in a stepwise or continuous manner in the intermediate phase of culture were performed under the four different conditions described below, with the condition that D-biotin was added to result in 0.1 mg/L and the above conditions other than the conditions for the dissolved oxygen concentration were employed.

(Shift Condition 1)

The initial dissolved oxygen concentration in the intermediate phase of culture was controlled at 2 ppm and maintained at 2 ppm for 40 hours. Then, the dissolved oxygen concentration was shifted to 2.5 ppm and maintained at 2.5 ppm until the end of culture. Specifically, the dissolved oxygen concentration was allowed to spontaneously decrease from the saturation concentration to 2 ppm within 0 to 8 hours after the initiation of culture, and controlled at 2 ppm within 8 to 48 hours and 2.5 ppm within 48 to 140 hours.

(Shift Condition 2)

The initial dissolved oxygen concentration in the intermediate phase of culture was controlled at 1 ppm, the level of 1 ppm was maintained for 8 hours, the controlled concentration was increased by 0.1 ppm every an hour such that the dissolved oxygen concentration was increased to 5 ppm within 40 hours, following which the level of 5 ppm was maintained until the end of culture. Specifically, the dissolved oxygen concentration was allowed to spontaneously decrease from the saturation concentration to 1 ppm within 0 to 9 hours after the initiation of culture, controlled at 1 ppm within 9 to 17 hours, increased by 0.1 ppm every an hour from 1 ppm to 5 ppm within 17 to 57 hours, and controlled at 5 ppm within 57 to 140 hours.

(Shift Condition 3)

The initial dissolved oxygen concentration in the intermediate phase of culture was controlled at 3 ppm and maintained at 3 ppm for 50 hours. Then, the dissolved oxygen concentration was shifted to 3.5 ppm and maintained at 3.5 ppm until the end of culture. Specifically, the dissolved oxygen concentration was allowed to spontaneously decrease from the saturation concentration to 3 ppm within 0 to 7 hours after the initiation or culture, and controlled at 3 ppm within 7 to 57 hours and 3.5 ppm within 57 to 140 hours.

(Shift Condition 4)

The initial dissolved oxygen concentration in the intermediate phase of culture was controlled at 2 ppm, the level of 2 ppm was maintained for 4 hours, the controlled concentration was increased by 0.1 ppm every two hours such that the dissolved oxygen concentration was increased to 7 ppm within 100 hours, following which the level of 7 ppm was maintained until the end of culture. Specifically, the dissolved oxygen concentration was allowed to spontaneously decrease from the saturation concentration to 2 ppm within 0 to 8 hours after the initiation of culture, controlled at 2 ppm within 8 to 12 hours, increased by 0.1 ppm every two hours from 2 ppm to 7 ppm within 12 to 112 hours, and controlled at 7 ppm within 112 to 140 hours.

Culture was carried out under the above four different conditions. The carotenoid concentration, the gluconic acid concentration, and the PHB content based on dry cells in each culture liquid at the end of culture (140 hours after the initiation of culture) were determined. Table 6 shows the results. The results were compared with those obtained by controlling the dissolved oxygen concentration at given levels (Table 4). Accordingly, it was found that a culture liquid having a high concentration of produced astaxanthin and a lower ratio of produced canthaxanthin can be obtained under any of the above conditions.

TABLE 6

Addition of 0.1 mg/L biotin

| | Condition for shifting dissolved oxygen concentration | | | |
|---|---|---|---|---|
| | Condition 1 | Condition 2 | Condition 3 | Condition 4 |
| Canthaxanthin mg/L | 154 | 166 | 39 | 41 |
| Astaxanthin mg/L | 796 | 863 | 752 | 800 |
| Adonixanthin mg/L | 156 | 162 | 214 | 212 |
| Canthaxanthin/Astaxanthin mass % | 19.3 | 19.2 | 5.2 | 5.1 |
| Adonixanthin/Astaxanthin mass % | 19.6 | 18.8 | 28.5 | 26.5 |
| Gluconic acid g/L | 8 | 11 | 13 | 6 |
| PHB mass % | 3 | 2 | 5 | 0 |

Example 4

*Paracoccus carotinifaciens* strain E-396 (FERM BP-4283) was subjected to mutation treatment with N-methyl-N'-nitro-N-nitrosoguanidine, and a colony taking on a strong red color was selected. The selected strain was cultured in a test tube. The mutant strain was selected with the condition that a decrease in pH of the culture liquid was small and the culture liquid took on a strong red color. The gluconic acid concentration and the carotenoid concentration in the test tube culture liquid of the selected mutant strain were determined, and the LG-7 mutant strain having low gluconic acid producing ability and high astaxanthin producing ability was selected.

A hundred milliliter of a medium (having the following composition: sucrose: 30 g/L; pharmamedia: 10 g/L; potassium dihydrogen phosphate: 0.8 g/L; dipotassium hydrogen phosphate: 4.2 g/L; calcium chloride dihydrate: 1 g/L; magnesium sulfate heptahydrate: 12 g/L; and iron sulfate heptahydrate: 1 g/L (pH 7.2)) was poured into a 500-ml cotton-plugged conical flask and sterilized in an autoclave at 121° C. for 20 minutes to prepare a flask containing the medium for seeding.

Next, 2.0 L of a medium (having the following composition: sucrose: 30 g/L; pharmamedia: 20 g/L; ammonium sulfate: 1.5 g/L; potassium dihydrogen phosphate: 1.5 g/L; disodium hydrogen phosphate dodecahydrate: 3.8 g/L; calcium chloride dihydrate: 0.1 g/L; magnesium sulfate heptahydrate: 4.5 g/L; iron sulfate heptahydrate: 5 g/L; L-monosodium glutamate monohydrate: 6 g/L; a silicone-based antifoamer: 1 g/L) was poured into a 5-L fermenter. Two fermenters were prepared in such manner. D-biotin was added to each fermenter to result in 1 mg/L, and each resultant was sterilized in an autoclave at 121° C. for 30 minutes.

A platinum loopful of the *Paracoccus* LG-7 strain selected above was inoculated into the medium for seeding in the flask prepared above, followed by rotary shaking culture at 100 rpm and 28° C. for 3 days. The culture liquids (80 mL each) were separately introduced into the fermenters for aerobic culture at 28° C. with an aeration volume of 1 vvm for 120 hours. pH was continuously controlled with 15% ammonia water so as to be maintained at 7.2 during culture. Sucrose (40 g) was added on the 1st, 2nd, 3rd, and 4th days of culture to prevent depletion of sucrose. In addition, the number of agitation rotations was changed (the lowest number of agitation rotations: 200 rpm) to control the concentration of dissolved oxygen in the culture liquid under the following two conditions.

(Shift Condition 5)

The initial dissolved oxygen concentration in the intermediate phase of culture was controlled at 2.5 ppm and maintained at 2.5 ppm for 35 hours. Then, the dissolved oxygen concentration was shifted to 3 ppm and maintained at 3 ppm until the end of culture. Specifically, the dissolved oxygen concentration was allowed to spontaneously decrease from the saturation concentration to 2.5 ppm within 0 to 8 hours after the initiation of culture, and controlled at 2.5 ppm within 8 to 43 hours and 3 ppm within 43 to 120 hours.

(Shift Condition 6)

The initial dissolved oxygen concentration in the intermediate phase of culture was controlled at 3.5 ppm, the level of 3.5 ppm was maintained for 4 hours, the controlled concentration was increased by 0.1 ppm every four hours such that the dissolved oxygen concentration was increased to 5 ppm within 60 hours, following which the level of 5 ppm was maintained until the end of culture. Specifically, the dissolved oxygen concentration was allowed to spontaneously decrease from the saturation concentration to 3.5 ppm within 0 to 7 hours after the initiation of culture, controlled at 3.5 ppm within 7 to 11 hours, increased by 0.1 ppm every four hours from 3.5 ppm to 5 ppm within 11 to 71 hours, and controlled at 5 ppm within 71 to 120 hours.

Culture was carried out under the above two different conditions. The carotenoid concentration, the gluconic acid concentration, and the PHB content based on dry cells in each culture liquid at the end of culture (120 hours after the initiation of culture) were determined. Table 7 shows the results. Table 7 also shows the culture results obtained by controlling the dissolved oxygen concentration in the intermediate phase of culture and that in the terminal phase of culture at a constant level of 4 ppm without the addition of biotin for comparison.

TABLE 7

| | Biotin concentration | | |
| --- | --- | --- | --- |
| | 1 mg/L | 1 mg/L | 0 |
| | Dissolved oxygen concentration condition | | |
| | Condition 5 | Condition 6 | 4 ppm (constant) |
| Canthaxanthin mg/L | 61 | 25 | 40 |
| Astaxanthin mg/L | 607 | 429 | 414 |
| Adonixanthin mg/L | 133 | 252 | 258 |
| Canthaxanthin/Astaxanthin mass % | 10.0 | 5.8 | 9.7 |
| Adonixanthin/Astaxanthin mass % | 21.9 | 58.7 | 62.4 |
| Gluconic acid g/L | 3 | 0 | 7 |
| PHB mass % | 17 | 18 | 35 |

Example 5

A hundred milliliter of a medium (having the following composition: sucrose: 20 g/L; corn steep liquor: 5 g/L; potassium dihydrogen phosphate: 0.54 g/L; dipotassium hydrogen phosphate: 2.78 g/L; calcium chloride dihydrate: 5 g/L; magnesium sulfate heptahydrate: 0.7 g/L; and iron sulfate heptahydrate: 3 g/L (pH 7.2)) was poured into a 500-ml cotton-plugged conical flask and sterilized by autoclave at 121° C., for 20 minutes to prepare a flask containing the medium for seeding.

Next, 2.0 L of a medium (having the following composition: glucose: 40 g/L; corn steep liquor: 30 g/L; ammonium sulfate: 0.5 g/L; potassium dihydrogen phosphate: 2.25 g/L; disodium hydrogen phosphate dodecahydrate: 5.7 g/L; calcium chloride dihydrate: 0.1 g/L; magnesium sulfate heptahydrate: 0.5 g/L; iron sulfate heptahydrate: 5 g/L; L-monosodium glutamate monohydrate: 6 g/L; and an alcohol-based antifoamer: 0.5 g/L) was poured into a 5-L fermenter. D-biotin was added to the fermenter to result in a concentration of 0.1 mg/L, and the resultant was sterilized in an autoclave at 121° C. for 30 minutes.

A platinum loopful of *Paracoccus* bacterial strain A-581-1 (FERM BP-4671) was inoculated into the medium for seeding in the flask prepared above, followed by rotary shaking culture at 150 rpm and 27° C. for 2 days. The culture liquid (80 mL) was poured into the fermenter for aerobic culture at 28° C. with an aeration volume of 1 vvm for 120 hours. pH was continuously controlled with 15% ammonia water so as to be maintained at 7.2 during culture. Glucose (30 g) was added on the 1st, 2nd, 3rd, and 4th days of culture to prevent depletion of glucose. In addition, the number of agitation rotations was changed (the lowest number of agitation rotations: 200 rpm) to control the concentration of dissolved oxygen in the culture liquid at 2 ppm in the intermediate phase of culture.

The carotenoid concentration, the gluconic acid concentration, and the PHB content based on dry cells at the end of culture were determined. Table 8 shows the results. Table 8 also shows the culture results obtained by controlling the dissolved oxygen concentration in the intermediate phase of culture at a constant level of 2 ppm without the addition of biotin for comparison.

TABLE 8

|  | Biotin concentration | |
|---|---|---|
|  | 0.1 mg/L | 0 |
|  | Dissolved oxygen concentration condition | |
|  | 2 ppm (constant) | 2 ppm (constant) |
| Canthaxanthin mg/L | 1.7 | 3.3 |
| Astaxanthin mg/L | 7.5 | 6.9 |
| Adonixanthin mg/L | 1.8 | 2.0 |
| Canthaxanthin/Astaxanthin mass % | 22.7 | 47.8 |
| Adonixanthin/Astaxanthin mass % | 24.0 | 29.0 |
| Gluconic acid g/L | 17 | 40 |
| PHB mass % | 18 | 29 |

Example 6

*Paracoccus* bacterial strain A-581-1 (FERM BP-4671) was subjected to ultraviolet irradiation for mutation treatment. Accordingly, a colony taking on a strong red color was selected. Carotenoids in the culture liquid of the selected strain were analyzed. Thus, the K-185 mutant strain having improved astaxanthin productivity was selected.

A hundred milliliter of a medium (having the following composition: sucrose: 30 g/L; corn steep liquor: 30 g/L; potassium dihydrogen phosphate: 1.5 g/L; disodium hydrogen phosphate dodecahydrate: 3.8 g/L; calcium chloride dihydrate: 5 g/L; magnesium sulfate heptahydrate: 0.7 g/L; and iron sulfate heptahydrate: 0.3 g/L; (pH 7.2)) was poured into a 500-ml cotton-plugged conical flask and sterilized b autoclave at 121° C. for 20 minutes to prepare a flask containing the medium for seeding.

Next, 2.0 L of a medium (having the following composition: glucose: 30 g/L; soybean meal: 20 g/L, ammonium sulfate: 1.5 g/L; potassium dihydrogen phosphate: 1.5 g/L; disodium hydrogen phosphate dodecahydrate: 3.8 calcium chloride dihydrate: 5 g/L; magnesium sulfate heptahydrate: 0.7 g/L; iron sulfate heptahydrate: 0.6 g/L; L-monosodium glutamate monohydrate: 6 g/L; and an ester-based antifoamer: 0.2 g/L) was poured into a 5-L fermenter. D-biotin was added to the fermenter to result in a concentration of 1 mg/L, and the resultant was sterilized in an autoclave at 121° C. for 30 minutes.

A platinum loopful of *Paracoccus* bacterial strain K-185 selected above was inoculated into the medium for seeding in the flask prepared above, followed by rotary shaking culture at 150 rpm and 27° C. for 2 days. The culture liquid (80 mL) was added to the fermenter for aerobic culture at 28° C. with an aeration volume of 1 vvm for 120 hours. pH was continuously controlled with 15% ammonia water so as to be maintained at 7.2 during culture. Glucose (30 g) was added on the 1st, 2nd, 3rd, and 4th days of culture to prevent depletion of glucose. In addition, the number of agitation rotations was changed (the lowest number of agitation rotations: 200 rpm) to control the concentration of dissolved oxygen in the culture liquid at 3.5 ppm in the intermediate phase of culture.

The carotenoid concentration, the gluconic acid concentration, and the PHB content based on dry cells at the end of culture were determined. Table 9 shows the results. Table 9 also shows the culture results obtained by controlling the dissolved oxygen concentration in the intermediate phase of culture at 3.5 ppm without the addition of biotin for comparison.

TABLE 9

|  | Biotin concentration | |
|---|---|---|
|  | 1 mg/L | 0 |
|  | Dissolved oxygen concentration condition | |
|  | 3.5 ppm (constant) | 3.5 ppm (constant) |
| Canthaxanthin mg/L | 2.2 | 6.0 |
| Astaxanthin mg/L | 39.0 | 35.2 |
| Adonixanthin mg/L | 29.6 | 28.9 |
| Canthaxanthin/Astaxanthin mass % | 5.6 | 17.0 |
| Adonixanthin/Astaxanthin mass % | 75.9 | 82.1 |
| Gluconic acid g/L | 19 | 38 |
| PHB mass % | 15 | 33 |

All publications, patents, and patent applications cited herein are incorporated herein by reference in their entirety.

The invention claimed is:

1. A method for producing carotenoids comprising:
   1) culturing a bacterial strain in a culture medium containing biotin at a concentration of 0.02 mg/L to 50 mg/L by addition of biotin to the culture medium, wherein the bacterial strain is a member of the genus *Paracoccus* and concurrently produces astaxanthin and canthaxanthin;
   2) increasing the concentration of dissolved oxygen in the culture medium in a stepwise or continuous manner during the intermediate phase of culture, wherein the concentration of dissolved oxygen in the culture medium at the beginning of the intermediate phase of culture before increasing the concentration is 2 ppm to 3.5 ppm, and the concentration of dissolved oxygen in the culture medium after increasing the concentration during the intermediate phase of culture is 3.5 ppm to 7 ppm, thereby producing a carotenoid-containing culture broth in which the ratio of the concentration of canthaxanthin to the concentration of astaxanthin in the culture broth at the end of the culture period is 8% by mass or less; and
   3) collecting the carotenoids from the carotenoid-containing culture broth.

2. The method of claim 1, wherein the concentration of gluconic acid in the carotenoid-containing culture broth at the end of the culture period is 30 g/L or less.

3. The method of claim 1, wherein a poly-β-hydroxybutyrate accumulation in the carotenoid-containing culture broth at the end of the culture period is 30% by mass or less based on dry cells.

4. The method of claim 1, wherein the bacterial strain is strain E-396 (FERM BP-4283) or strain A-581-1 (FERM BP-4671).

5. The method of claim 1, wherein the bacterial strain is *Paracoccus carotinifaciens*.

* * * * *

SEQUENCE LISTING

```
<160> NUMBER OF SEQ ID NOS: 1

<210> SEQ ID NO 1
<211> LENGTH: 1452
<212> TYPE: DNA
<213> ORGANISM: Paracoccus carotinifaciens
<220> FEATURE:
<221> NAME/KEY: misc_feature
<222> LOCATION: (1350)..(1350)
<223> OTHER INFORMATION: n is a, c, g, or t

<400> SEQUENCE: 1
agtttgatcc tggctcagaa cgaacgctgg cggcaggctt aacacatgca agtcgagcga       60
gaccttcggg tctagcggcg gacgggtgag taacgcgtgg gaacgtgccc ttctctacgg      120
```

```
aatagccccg ggaaactggg agtaataccg tatacgccct ttgggggaaa gatttatcgg      180
agaaggatcg gccgcgttg  gattaggtag ttggtgggt  aatggccac  caagccgacg      240 atccatagct ggtttgagag gatgatcagc cacactggga ctgagacacg gcccagactc      300
ctacgggagg cagcagtggg gaatcttaga caatgggggc aaccctgatc tagccatgcc      360
gcgtgagtga tgaaggcctt agggttgtaa agctctttca gctgggaaga taatgacggt      420
accagcagaa gaagccccgg ctaactccgt gccagcagcc gcggtaatac ggaggggggct     480 agcgttgttc ggaattactg ggcgtaaagc gcacgtaggc ggactggaaa gtcagaggtg      540
aaatcccagg gctcaacctt ggaactgcct ttgaaactat cagtctggag ttcgagagag      600
gtgagtggaa ttccgagtgt agaggtgaaa ttcgtagata ttcggaggaa caccagtggc      660
gaaggcggct cactggctcg atactgacgc tgaggtgcga aagcgtgggg agcaaacagg      720
attagatacc ctggtagtcc acgccgtaaa cgatgaatgc cagacgtcgg caagcatgct      780
tgtcggtgtc acacctaacg gattaagcat tccgcctggg gagtacggtc gcaagattaa      840
aactcaaagg aattgacggg ggcccgcaca agcggtggag catgtggttt aattcgaagc      900
aacgcgcaga accttaccaa cccttgacat ggcaggaccg ctggagagat tcagctttct      960
cgtaagagac ctgcacacag gtgctgcatg gctgtcgtca gctcgtgtcg tgagatgttc     1020
ggttaagtcc ggcaacgagc gcaacccacg tccctagttg ccagcaattc agttgggaac    1080
tctatggaaa ctgccgatga taagtcggag gaaggtgtgg atgacgtcaa gtcctcatgg    1140
gccttacggg ttgggctaca cacgtgctac aatggtggtg acagtgggtt aatcccaaa    1200 agccatctca gttcggattg tcctctgcaa ctcgagggca tgaagttgga atcgctagta    1260
atcgcggaac agcatgccgc ggtgaatacg ttcccgggcc ttgtacacac cgcccgtcac    1320
accatgggag ttggttctac ccgacgacgn tgcgctaacc ttcgggggc  aggcggccac    1380 ggtaggatca gcgactgggg tgaagtcgta acaaggtagc cgtagggaa  cctgcggctg    1440 gatcacctcc tt                                                          1452
```